United States Patent [19]

Ishii

[11] Patent Number: 4,538,593
[45] Date of Patent: Sep. 3, 1985

[54] CONNECTING DEVICE

[75] Inventor: Fumiaki Ishii, Tokyo, Japan

[73] Assignee: Olympus Optical Co. Ltd., Tokyo, Japan

[21] Appl. No.: 563,646

[22] Filed: Dec. 19, 1983

[30] Foreign Application Priority Data

Dec. 28, 1982 [JP] Japan .............................. 57-202530[U]

[51] Int. Cl.³ .............................................. A61B 1/00
[52] U.S. Cl. ......................................................... 128/4
[58] Field of Search ...................................... 128/4–11

[56] References Cited

U.S. PATENT DOCUMENTS

| 3,980,078 | 9/1976 | Tominaga | 128/4 |
| 4,216,767 | 8/1980 | Aoshiro | 128/6 |
| 4,241,729 | 12/1980 | Aoshiro | 128/4 |
| 4,261,343 | 4/1981 | Ouchi et al. | 128/4 |

Primary Examiner—William H. Grieb
Attorney, Agent, or Firm—Frishauf, Holtz, Goodman & Woodward

[57] ABSTRACT

A connecting device has a first connector attached to a endoscope and a second connector communicating with a gas supply unit and adapted to be connected to the first connector. The first connector has a communication pipe having lower and upper ends communicating with the inside and outside of the endoscope, respectively. A valve plug is disposed in the pipe to be movable between the closing and opening positions. A rotating body is fitted to the outside of the upper end portion of the pipe to be rotatable between the first and second positions. The valve plug is moved in conjunction with the rotation of the rotating body. The second connector has an engaging slit adapted to engage a first retainer projecting from the pipe when the second connector is rotated after being fitted to the first connector. A second retainer projects inward from the second connector and is adapted to engage with an engaging portion of the rotating body when the second connector is fitted to the first connector. The second retainer rotates the rotating body to move the valve plug from the closing position to the opening position when the second connector is rotated from the fitting position.

8 Claims, 11 Drawing Figures

CONNECTING DEVICE

BACKGROUND OF THE INVENTION

The present invention relates to a connecting device for use in connecting a high-pressure gas supply unit to an endoscope, in checking the endoscope for gastightness.

In general, all parts of an endoscope; including an operating section and a universal cord coupled thereto, as well as an insert section, are in danger of being contaminated during use. Therefore, the entire endoscope is made gastight, and, after use, is immersed in a medical fluid for disinfection. During disinfection, if the insert section formed of a flexible tube or the universal cord has pinholes or cracks; after disinfection, the disinfectant or wash water may possibly soak into the endoscope, damaging optical system, etc.

Conventionally, therefore, the operating section or other sections of the endoscope are provided with a communicating section for connecting the inside and outside of the endoscope. Gas is fed into the endoscope through the communicating section to pressurize the interior of the endoscope. Then, the endoscope is immersed in water to be checked for the leakage of the gas in the form of bubbles. In so doing, a gas supply unit is connected to the endoscope, to supply the gas thereto. In connecting the endoscope and the gas supply unit, a mouthpiece which is attached to one end of a hose connected to the gas supply unit is press-fitted onto the communicating section, with the aid of an O-ring on the inner peripheral surface of the mouthpiece. In this case, however, if an unexpected external force is applied to the endoscope or hose, in the middle of the leakage check, the mouthpiece may be easily disconnected from the communicating section.

Thereupon, a connecting device for connecting a gas supply unit to a gastight endoscope is conventionally proposed, which device comprises a communicating section for connecting the inside and outside of the endoscope; a retainer protruding from the outer peripheral surface of the communicating section; and a gas supply side connector having an engaging slit which engages with the retainer, being connected to a hose of the gas supply unit, and being securely connected to the communicating section, by engaging the retainer with the engaging slit (Japanese Utility Model Application No. 57-113549).

In this prior art connecting device, the communicating section and the connector are connected in the following manner. First, the retainer is fitted into the engaging slit of the connector which is located on the communicating section. Then, the connector is rotated in relation to the communicating section so that the retainer is located at the extreme end of the engaging slit. Thereafter, the connector is further rotated so that the retainer moves in relation to the communicating section, pressed by the extreme end portion of the engaging slit. As the retainer moves in this manner, a valve in the communicating section is opened. As a result, the interior of the endoscope is connected to the gas supply unit. In removing the connector from the communicating section, the connector is rotated in the direction opposite to the direction of the connection, until the other end of the engaging slit abuts against the retainer. In this position, the connector is ready for removal from the communicating section. In closing the valve, the connector is further rotated so that the retainer is moved by the other end of the engaging slit.

In the connecting device of this type, however, the connecting function of the connector is not entirely associated with the valve's opening and closing actions. In the position where the retainer is in contact with the other end of the engaging slit of the connector, the connector is ready for the removal from the communicating section although the valve is open. Therefore, if an unexpected force is applied to the connector in the middle of the leakage check, the connector will possibly rotate to the aforesaid position to be disengaged from the communicating section. Since the valve is then open, the water for the leakage check will enter the endoscope through the communicating section. Since the retainer interlocking with the valve projects from the communicating section, an external force may act on the retainer to move the same, thereby opening the valve during, e.g., transportation of the endoscope. If a user, unaware of these circumstances, washes the endoscope, the aforementioned trouble will occur.

SUMMARY OF THE INVENTION

The present invention has been contrived in view of these circumstances, and is intended to provide a connecting device which is capable of securely connecting an endoscope and a gas supply unit, and which has improved safety features, in that the gas supply unit will never be disconnected from the endoscope when a valve is open, and the valve cannot be easily opened when the endoscope and the gas supply unit are not connected.

To attain the above object, a connecting device according to the invention comprises a first connector attached to an endoscope, and a second connector communicating with a gas supply unit and adapted to be connected to the first connector. The first connector includes: a communication pipe which is attached to the endoscope, and which has first and second ends respectively communicating with the inside and outside of the endoscope, and the second end portion of the communication pipe extending outward from the endoscope; a first retainer projecting outward from the second end portion of the communication pipe; a ring-shaped rotating body which is so fitted to the second end portion of the communication pipe as to be rotatable between first and second positions, and which has an engaging portion on the outer peripheral surface thereof; and a valve plug which is disposed in the communication pipe and which moves in conjunction with the rotation of the rotating body, between a closing position where it closes the communication pipe and an opening position where it allows gas to flow through the communication pipe. The second connector includes a substantially ring-shaped housing to be fitted to the first connector in a gastight manner, for rotation relative to the first connector; and a second retainer projecting inward from the housing and being capable of engaging with the engaging portion of the rotating body. As the housing is rotated after it is put on the first connector, the second retainer rotates the rotating body by engaging with the engaging portion, thereby moving the valve plug to the opening position. The second retainer can be engaged with or disengaged from the engaging portion of the rotating body only when the valve plug is in the closing position. The housing has an engaging slit capable of engaging with the first retainer. The engaging slit engages with the first retainer when the housing is rotated after it has been fitted to the first connector, thereby preventing the housing from coming off of the first connector.

According to the connecting device of the invention, the valve plug is operated in conjunction with the rotation of the rotating body, and the rotating body is rotated by the second retainer which protrudes from the housing of the second connector. The second retainer can be engaged with or disengaged from the engaging portion of the rotating body only when the valve plug is in the closing position, that is, only when the rotating body is in the first position. In other words, the second retainer cannot be removed from the rotating body when the valve body is in the opening position. When the valve plug is in the opening position, the first retainer is in engagement with the engaging slit of the housing. Accordingly, the second connector will never be disconnected from the first connector when the valve plug is in the opening position. Since the rotating body interlocking with the valve plug is ring-shaped, it will never be easily rotated by any unexpected external force. Therefore, the valve plug will never open readily, when the first and second connectors are not connected.

BRIEF DESCRIPTION OF THE DRAWINGS

FIGS. 2 to 11 show a connecting device according to one embodiment of the present invention, in which

DETAILED DESCRIPTION OF THE PREFERRED EMBODIMENT

One embodiment of the present invention will now be described in detail with reference to the accompanying drawings.

Figure 1:
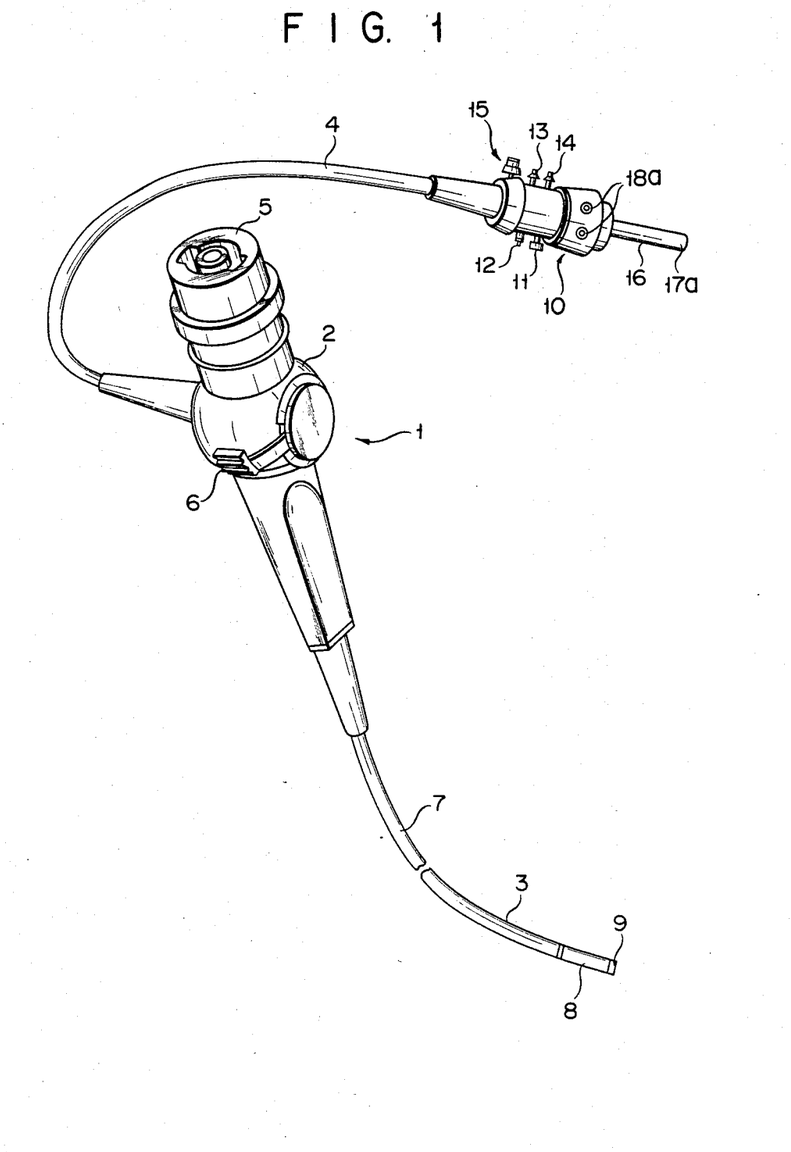
FIG. 1 is a perspective view of a gastight endoscope.

In FIG. 1, numeral 1 designates an endoscope of an entirely gastight structure. This endoscope 1 comprises an operating section 2, an insert section 3 formed of an elongate flexible tube connected to the operating section 2, and a universal cord 4. The operating section 2 is provided with an eyepiece portion 5, an operating knob 6, etc. The insert section 3 is provided with a flexible tube portion 7 and a distal end portion 9 attached to the distal end of the flexible tube portion 7 by means of a curved tube portion 8. A connecting section 10 connected to a light source unit (not shown) is attached to the extreme end of the universal cord 4. The connecting section 10 is provided on its outer peripheral wall with an air/water feeding mouthpiece 11, a $CO_2$ feeding mouthpiece 12, a suction mouthpiece 13, an earth terminal 14, and a first connector 15 of a connecting device of the present invention mentioned later. A light guide mouthpiece 16 adapted to be inserted into a socket of the light source unit protrudes from the distal end face of the connecting section 10. The extreme end edge is formed into a rounded portion 17a for ease of insertion into the socket. Numeral 18a designates connecting pins.

Figure 2:
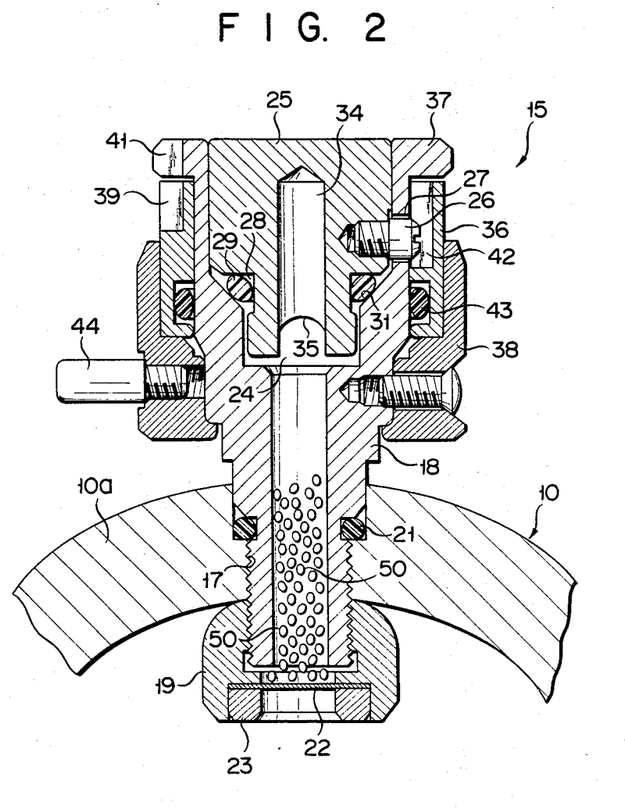
FIG. 2 is a longitudinal sectional view of a first connector.

The first connector 15, which is constructed as shown in FIG. 2, includes a stepped communication pipe 18. The lower end portion of the communication pipe 18, which is reduced in diameter, is passed through a mounting hole 17 bored through an outer wall 10a of the connecting section 10. The lower end of the communication pipe 18 is clamped by a fixing nut 19, so that the outer wall 10a is secured between the nut 19 and the stepped portion of the communication pipe 18. Thus, the communication pipe 18 is secured to the connecting section 10. An O-ring 21 is interposed between the outer peripheral surface of the lower end portion of the communication pipe 18 and the mounting hole 17, thereby keeping the combined structure gastight. The upper end portion of the communication pipe 18 projects outward from the connecting section 10. Thus, the interior of the connecting section 10, that is, the interior of the endoscope 1, communicates with the outside by means of the communication pipe 18. A sheetlike porous member 22 is attached to the internal end of the fixing nut 19 by means of a holding ring 23. The porous member 22 entirely covers the lower end opening of the communication pipe 18, so that the communication pipe 18 communicates with the interior of the endoscope 1 through the porous member 22. The porous member 22 is formed of a material which is permeable to gas, though not to liquid, for example a polytetrafluoroethylene having a great numer of pores with a diameter of about 10 microns.

Figure 3:
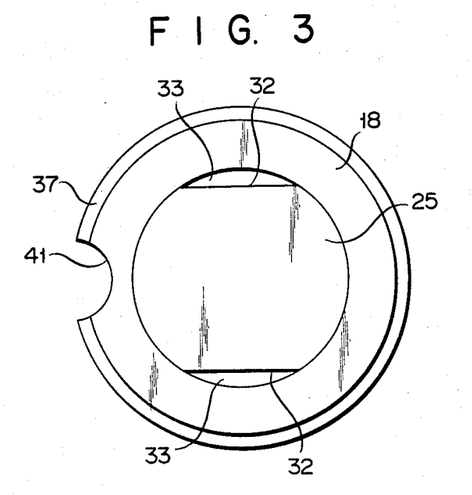
FIG. 3 is a schematic plan view of the first connector.
Figure 4:
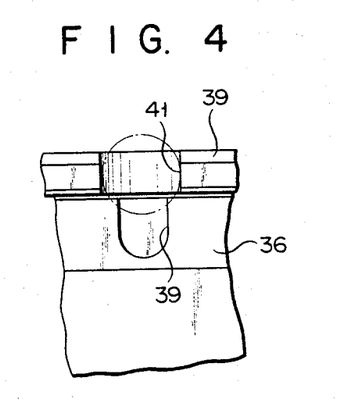
FIG. 4 is a schematic view showing the principal portion of the first connector.
Figure 9:
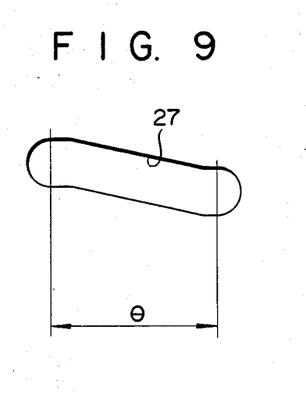
Figure 11:
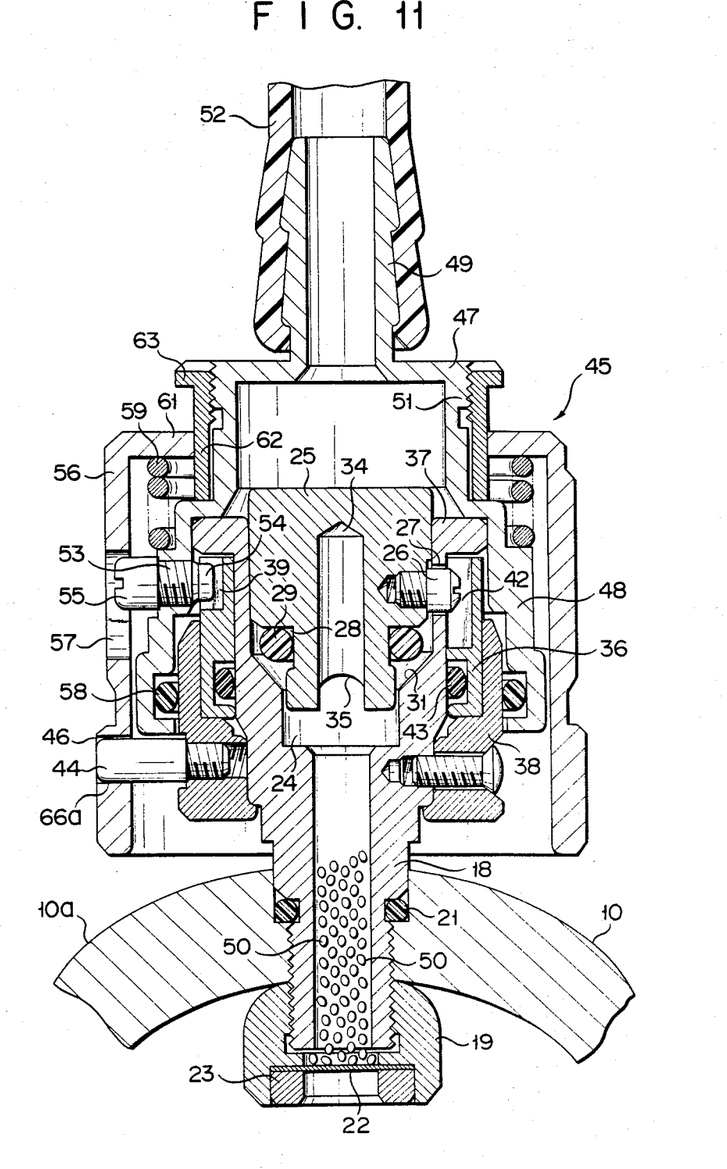
FIG. 11 is a longitudinal sectional view showing the first and second connectors after completion of the connection.

The upper end portion of the communication pipe 18 projecting outward from the connecting section 10 has inside and outside diameters greater than those of the lower end portion thereof. A valve plug 25 of a substantially stepped cylindrical shape is fitted into a valve chest 24 defined within the upper end portion of the communication pipe 10 so that the valve plug 25 can move up and down along the axial direction of the communication pipe and rotate, as well. A cam receiving pin 26 is screwed to the side wall of the valve plug 25. The cam receiving pin 26 is engagedly fitted into a cam slot 27 within the wall of the communication pipe 18, and projects outward from the communication pipe 18 through the cam slot. As shown in FIG. 9, the cam slot 27 is inclined against the axis of the communication pipe 18, covering an angular range of $\theta = 90°$. As the cam receiving pin 26 moves along the cam slot 27, the valve plug 25 moves along the axis of the communication pipe 18, while rotating within the valve chest 24. An annular ring retaining groove 28 is formed on the outer peripheral surface of the lower end portion of the valve plug 25. An O-ring 29 is fitted into the ring retaining groove 28. The O-ring 29 abuts against a valve seat 31 of the valve chest 24 to close the communication pipe 18 when the valve plug 25 is in its lowest position (closing position), as shown in FIG. 2. When the valve plug 25 is located in its elevated position (opening position), as shown in FIG. 11, the O-ring 29 leaves the valve seat 31 to open the communication pipe 18. As shown in FIG. 3, a pair of cuts 32 are formed on the outer peripheral surface of the large-diameter portion of the valve plug 25 which is located above the O-ring 29. Thus, a gas passage 33 is defined between each of the cuts 32 and the inner peripheral surface of the valve chest 24. A blind bore 34 coaxial with the valve plug 25 extends from the lower end face of the valve plug 25 toward the upper end thereof. An indentation 35 for gas release is formed in the open end portion of the side wall of the blind bore 34. The indentation 35 defines a gas passage when the valve plug 25 is in the opening position shown in FIG. 11. An annular rotating body 36 is placed on the upper end portion of the outer peripheral surface of the communication pipe 18. This rotating body 36 is supported by a flange 37 on the outer periphery of the upper end of the communication pipe 18 and a cover ring 38 which is screwed to the communication pipe 18. Thus, the rotating body 36 can rotate around the communication pipe 18 in a fixed position, without moving along the axis of the communication pipe 18. The cover ring 38 covers the lower half of the rotating body 36. An engaging portion or indentation 39 is formed on the exposed portion of the outer peripheral surface of the rotating body 36, axially extending from the upper end edge thereof. An indentation 41 capable of corresponding to the engaging portion 39 is formed on the flange 37. A groove 42 engaging the cam receiving pin 26 is formed on the inner peripheral surface of the rotating body 36. The groove 42 is elongated along the axis of the communication pipe 18. When the rotating body 36 is rotated, the valve plug 25 is moved thereby through the medium of the pin 26. Thus, the valve plug 25 moves rotating between the closing position shown in FIG. 2 and the opening position shown in FIG. 11 along the axis of the communication pipe 18. When the valve plug 25 is in the closing position, the rotating body 36 is located in a first position shown in FIG. 2. When the valve plug 25 is in the opening position, the rotating body 36 is located in a second position shown in FIG. 11. In the first position, the engaging portion 39 of the rotating body 36 faces and is connected with the indentation 41 of the flange 37, as shown in FIGS. 2 and 4. An O-ring 43 is interposed between the communication pipe 18 and the rotating body 36, for gastight construction.

A first retainer 44 in the form of a pin is attached to the cover ring 38 and extends outward. The first retainer 44 is adapted to engage with an engaging slit 46 of a second connector 45 of the connecting device (to be mentioned later).

The lower end portion of the communication pipe 18 is filled with a number of spherical hygroscopic materials 50 composed of, for example, silicagel.

Figure 5:
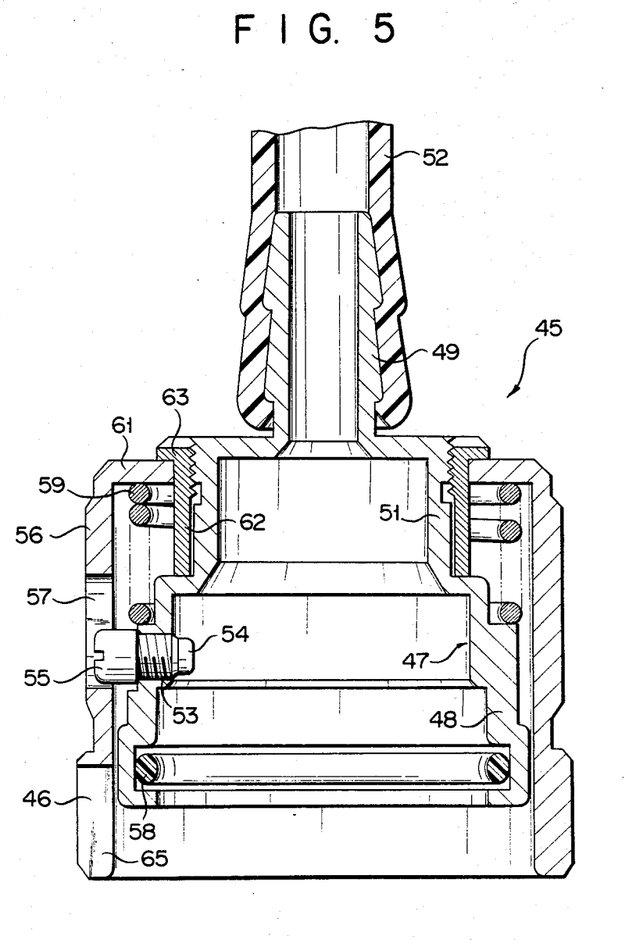
FIG. 5 is a longitudinal sectional view of a second connector.

The first connector 15 constructed in this manner is detachably connected to the second connector 45, as shown in FIG. 5. In FIG. 5, numeral 47 designates a connecting mouthpiece, which includes a large-diameter portion 48 adapted to be fitted on the outer peripheral surface of the first connector 15, a small-diameter portion 49, and a medium-diameter portion 51 connecting these two portions 48 and 49. A hose 52 connected to a high-pressure gas supply unit (not shown) is fitted onto the small-diameter portion 49 for connection. A second retainer 53 is attached to the wall of the large-diameter portion 48, and it engages the engaging portion 39 when the second connector 45 is fitted on the first connector 15. The second retainer 53 is formed of a screw member which penetrates the wall of the large-diameter portion 48. A projecting portion 54 of the second retainer 53, which projects inward from the wall of the large-diameter portion 48, is adapted to engage with the engaging portion 39. An outwardly projecting head portion 55 of the second retainer 53 is fitted into a slot 57 formed in the wall of a connecting cylinder 56 (to be mentioned later). A sealing O-ring 58, which is adapted to be fitted onto the cover ring 38 of the first connector 15, is attached to the inner periphery of the open end portion of the large-diameter portion 48.

The connecting cylinder 56 is fitted onto the outer peripheral surface of the connecting mouthpiece 47, for axial movement. As mentioned above, the head portion 55 of the second retainer 53 is inserted into the slot 57 which extends axially in the wall of the connecting cylinder 56. Thus, the connecting cylinder 56 may only move axially, within the range of the length of the slot 57. The connecting cylinder 56 has a ring-shaped spring retainer 61 projecting radially inward from its upper end, and is urged axially upward by a compression spring 59 interposed between the spring retainer 61 and the connecting mouthpiece 47. Normally, the connecting cylinder 56 is positioned in such a manner that its spring retainer 61 abuts against a flange 63 of a holding ring 62 which is screwed onto the outer peripheral surface of the medium-diameter portion 51 of the connecting mouthpiece 47, as shown in FIG. 5.

Figure 10:
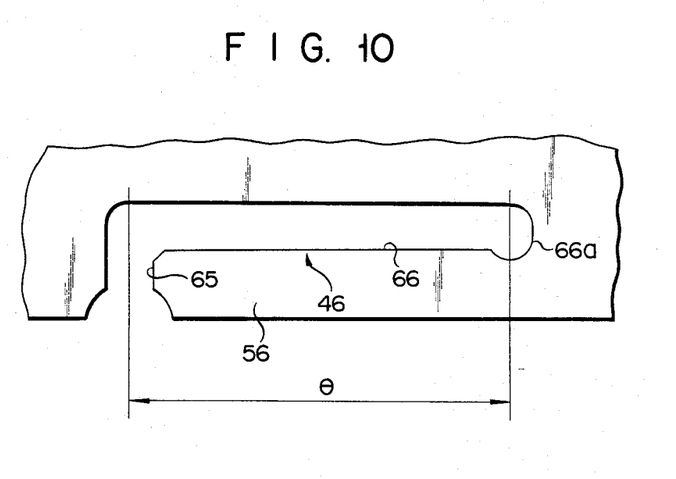

The engaging slit 46 capable of engaging the first retainer 44, as shown in FIG. 10, is formed in the lower end portion of the peripheral wall of the connecting cylinder 56. The engaging slit 46 is formed of a vertical slit 65 and a horizontal slit 66 continuous therewith. The vertical slit 65 extends along the axis of the connecting cylinder 56 and opens to the lower end edge thereof. When the connecting cylinder 56 is put onto the first connector 15, the first retainer 44 is inserted into the vertical slit 65. The horizontal slit 66 is elongated along the circumference of the connecting cylinder 56 from the upper end of the slit 65, and the angular range $\theta$ of the horizontal slit 66 is equal to that of the cam slot 27.

The operation of the connecting device of the aforementioned construction will now be described. In the state before connection, the valve plug 25 of the first connector 15 is located in the closing position shown in FIG. 2. In the closing position, the valve plug 25 is pushed in the valve chest 24, so that the O-ring 29 is firmly pressed against the valve seat 31 to close the communication pipe 18. At this time, the rotating body 36 is located in the first position shown in FIG. 2, so that the engaging portion 39 of the rotating body 36 faces the indentation 41 of the flange 37.

Figure 6:
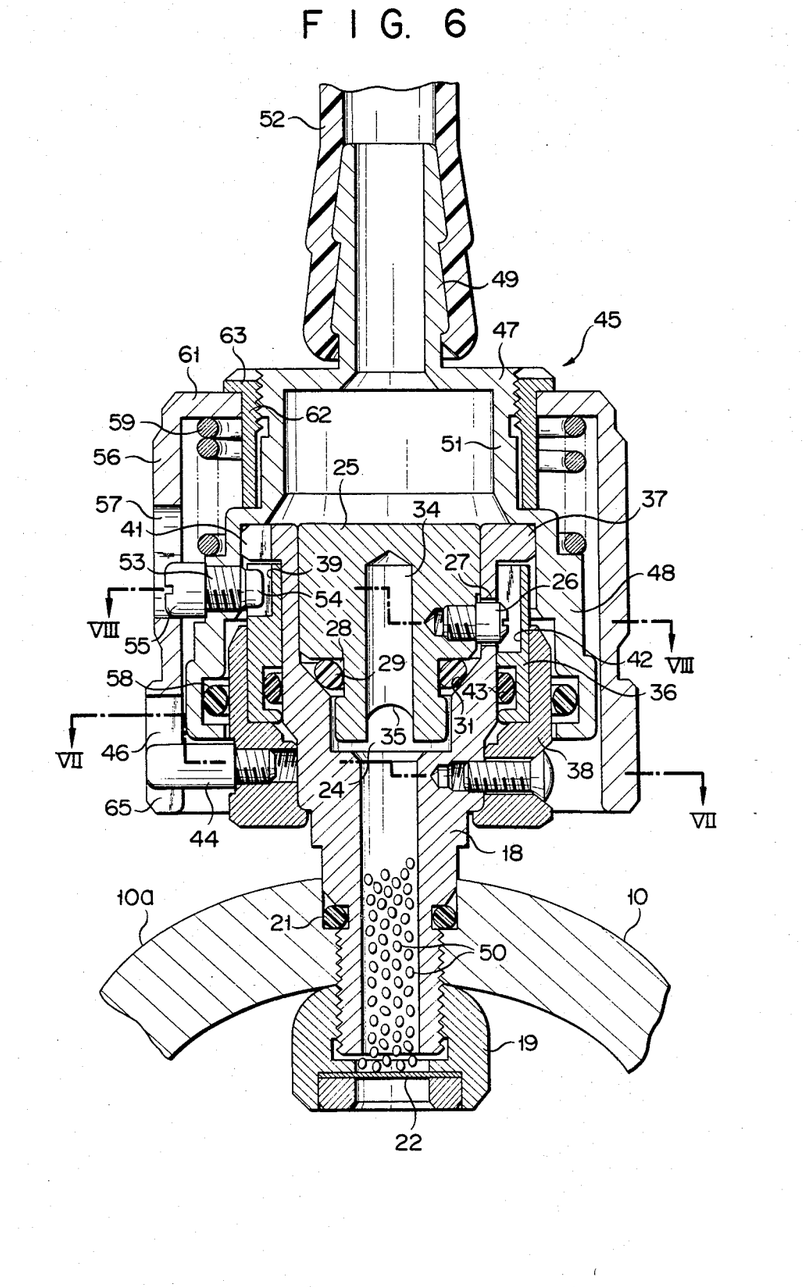
FIG. 6 is a longitudinal sectional view showing the first and second connectors coupled to each other.
Figure 7:
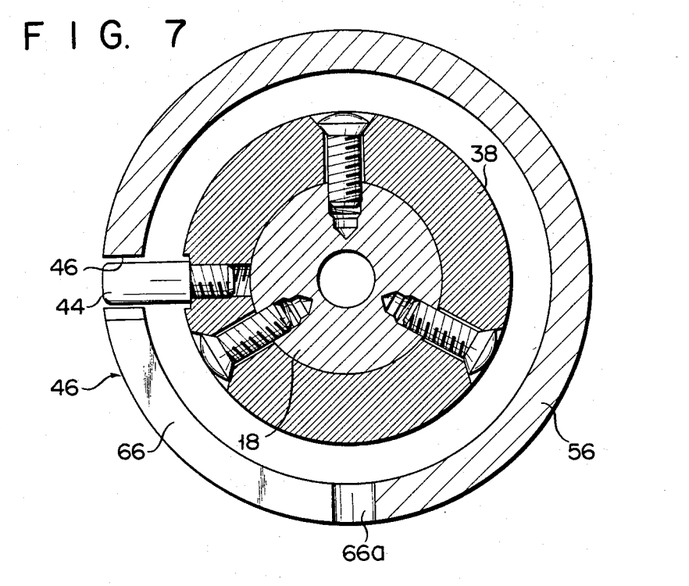
FIG. 7 is a sectional view taken along line VII—VII of FIG. 6.
Figure 8:
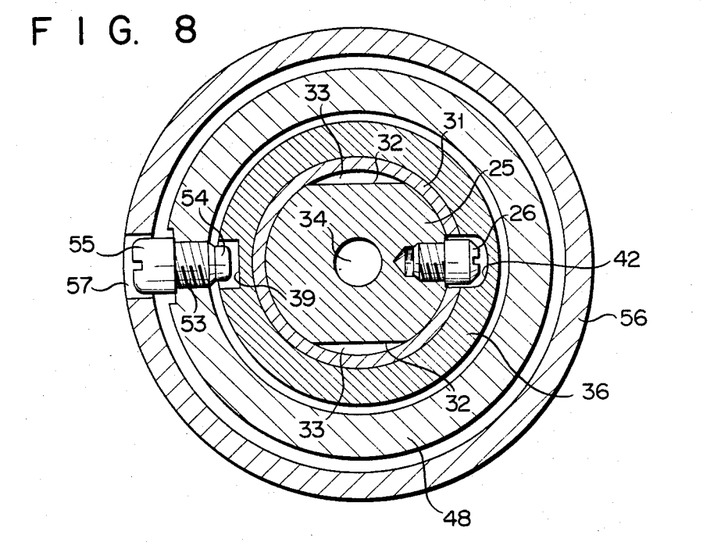
FIG. 8 is a sectional view taken along line VIII—VIII of FIG. 6, FIGS. 9 and 10 are schematic views showing different principal portions of the connecting device.

In checking the endoscope 1 for leakage, the second connector 45 is first connected to the first connector 15, in the following manner. The connecting mouthpiece 47 is put on the first connector 15 so that the first retainer 44 is fitted into the vertical slit 65 of the engaging slit 46 of the connecting cylinder 56, as shown in FIG. 6. At this time, the projecting portion 54 of the second retainer 53 is fitted into the engaging portion 39 of the rotating body 36, passing through the indentation 41. Then, the connecting cylinder 56 is pressed down against the urging force of the compression spring 59 so that the first retainer 44 is located in the upper end of the vertical slit 65. Thereupon, the whole second connector 45 is rotated about 90° in the clockwise direction to establish the state shown in FIG. 11. Specifically, the first retainer 44 reaches through the horizontal slit 66 and engages with the innermost recess 66a of the horizontal slit 66. As the second connector 45 rotates, the rotating body 36 engaged with the second retainer 53 at its engaging portion 39 also rotates to reach the second position shown in FIG. 11. Since the groove 42 of the rotating body 36 is engaged with the cam receiving pin 26 which is attached to the valve plug 25, the valve plug 25 rotates in conjunction with the rotating body 36. Also, since the cam receiving pin 26 engages with the cam slot 27 which is inclined against the axis of the communication pipe 18, the valve plug 25 axially moves upward, rotating in such a way as to reach the opening position shown in FIG. 11. In the course of the spiral ascent of the valve plug 25, the O-ring 29 on the valve plug 25 leaves the valve seat 31. During the initial stage of the ascent, however, the O-ring 29 only returns to its original form, without entirely leaving the valve seat 31. In the final stage, the O-ring 29 is entirely removed from the valve seat 31 to open the communication pipe 18. As a result, the hose 52 connected to the connecting mouthpiece 47 communicates with the interior of the endoscope 1 through the gas passages 33, the space between the O-ring 29 and the valve seat 31, and the releasing indentation 35.

In the state shown in FIG. 11, the first retainer 44 engages with the horizontal slit 66 of the engaging slit 46. In the second position, the engaging portion 39 of the rotating body 36 is located off the indentation 41 of the flange 37, and the projecting portion 54 of the second retainer 53 is prevented by the flange 37 from being disengaged from the engaging portion 39. Thus, the second connector 45 is securely connected to the first connector 15, being prevented from coming off the same.

Subsequently, high-pressure gas is supplied from the gas supply unit (not shown) by means of the hose 52, and is fed into the endoscope 1 through the communication pipe 18, to pressurize the interior of the endoscope 1. If the endoscope 1 has pinholes or cracks in any portions thereof, the high-pressure gas in the endoscope 1 will leak from the defective portions. Therefore, the defective portions can be detected by immersing the endoscope 1 in water to visually identify the gas which is leaking in the form of bubbles.

After the leakage check, the endoscope 1 is taken out of the water, and the second connector 45 is removed from the first connector 15. In removing the second connector 45, the gas supply from the gas supply unit is first stopped, and the second connector 45 is then rotated about 90° in the direction opposite to the direction of the connection. As a result, the first retainer 44 moves to the upper end portion of the vertical slit 66 of the engaging slit 46, and the connecting cylinder 56 is automatically raised by the urging force of the compression spring 59, returning to the position shown in FIG. 6. The rotating body 36 rotates to the second position shown in FIG. 6, so that the engaging portion 39 faces the indentation 41 of the flange 37. Thus, the second connector 45 becomes ready for the removal from the first connector 15. As the rotating body 36 rotates in this manner, the pin 26 engaging the groove 42 of the rotating body 36 presses down the valve plug 25 along the cam slot 27 to the closing position. As a result, the valve plug 25 presses the O-ring 29 against the valve seat 31 to close the communication pipe 18. The closing action of the valve plug 25 is completed before the first retainer 44 reaches the vertical slit 65. Therefore, the communication pipe 18 is closed whenever the second connector 45 is ready for the removal.

According to the connecting device constructed in this manner, the opening and closing actions of the valve plug 25 are only in conjunction with the connecting and removing operations of the first and second connectors 15, 45. Accordingly, the valve plug 25 is located in the closing position whenever the second connector 45 is ready for removal from the first connector 15. Thus, the second connector 45 may never be removed when the valve plug 25 is in the opening position. The connection between the first and second connectors 15, 45 is maintained, with high reliability, by the first and second retainers 44, 53. The rotating body 36, which interlocks with the valve plug 25, is put on the outer peripheral surface of the communication pipe 18 in a depressed manner, and is rotated by the second retainer 53 which protrudes from the second retainer 53. When the two connectors 15, 45 are not connected, therefore, the rotating body 36 is hardly affected by any external force, so that the valve plug 25 will never open easily.

It is to be understood that the present invention is not limited to the embodiment described above, and that various changes and modifications may be effected therein by one skilled in the art, without departing from the scope or spirit of the invention. For example, the first connector 15 may be attached to the operating section of the endoscope, instead of being attached to the connecting section. The pin 26 and the first and second retainers 44, 53, which are described as being of a screw type in the above embodiment, may be replaced with stud-type counterparts.

What is claimed is:

1. A connecting device for connecting a gastight endoscope to a gas supply unit comprising:
   a first connector attached to the endoscope, said first connector including:
   a communication pipe which is secured to the endoscope, and which has first and second ends communicating with the inside and outside of the endoscope, respectively, and the second end portion extending outward from the endoscope,
   a first retainer projecting outward from the second end portion of the communication pipe,
   a ring-shaped rotating body fitted to the outside of the second end portion of the communication pipe to be rotatable between first and second positions, and having an engaging portion on the outer peripheral surface thereof, and
   a valve plug disposed in the communication pipe to be movable in conjunction with the rotation of the rotating body between a closing position where the valve plug closes the communication pipe and an opening position where the valve plug allows gas to flow through the communication pipe, the valve plug being located in the closing position when the rotating body is in the first position and in the opening position when the rotating body is in the second position; and
   a second connector communicating with the gas supply unit and adapted to be connected to the first connector, said second connector including:
   a substantially ring-shaped housing which is to be fitted to the first connector in a gastight manner, for rotation relative to the first connector, the housing having an engaging slit adapted to engage the first retainer when the housing is rotated after being fitted to the first connector, so that the housing is prevented from coming off of the first connector, and a second retainer projecting inward from the housing, the second retainer being adapted to engage with the engaging portion of the rotating body when the housing is fitted to the first connector, and to rotate the rotating body to move the valve plug from the closing position to the opening position when the housing is rotated from the fitting position, the second retainer being allowed to engage with and disengage from the engaging portion only when the rotating body is in the first position.

2. The connecting device according to claim 1, wherein said communication pipe has an elongate cam slot formed in the peripheral wall of the second end portion thereof and inclined against the axis of the communication pipe; the rotating body has a groove formed on the inner peripheral surface thereof and extending along the axis of the communication pipe; and the valve plug has a cam receiving pin projecting therefrom to the outside of the communication pipe through the cam slot and engaging with the groove, the cam receiving pin being adapted to be moved by the rotating body along the cam slot, thereby moving the valve plug along the axis of the communication pipe, as the rotating body rotates.

3. The connecting device according to claim 2, wherein said communication pipe has a ring-shaped flange projecting outward from the second end thereof; one end edge of the rotating body abuts against the flange; and the engaging portion of the rotating body is composed of a groove on the outer peripheral surface of the one end portion of the rotating body, extending along the axis of the communication pipe and opening to the one end edge of the rotating body; and the flange having an indentation which is so located as to face the engaging portion of the rotating body when the rotating body is in the first position.

4. The connecting device according to claim 3, wherein said first connector has a ring-shaped cover attached to the second end portion of the communication pipe and covering the outer periphery of the other end portion of the rotating body, whereby the rotating body is restrained from moving axially, with the aid of the flange of the communication pipe.

5. The connecting device according to claim 4, wherein said housing has a substantially ring-shaped connecting mouthpiece to be fitted to the first connector; and the second retainer projects inward from the connecting mouthpiece and being adapted to engage with the engaging portion of the rotating body through the indentation of the flange when the connecting mouthpiece is fitted to the first connector.

6. The connecting device according to claim 5, wherein said housing has a connecting cylinder which is fitted to the outside of the connecting mouthpiece to be movable along the axis of the communication pipe; and the engaging slit is formed in the wall of the connecting cylinder and composed of a vertical slit and a horizontal slit continuous therein, the vertical slit extending along the axis of the communication pipe and one end of the vertical slit opening to one end edge of the connecting cylinder located on the first end side of the communication pipe, and the horizontal slit extending from the other end of the vertical slit along the circumference of the connecting cylinder; the connecting cylinder has a slot extending along the axis of the communication pipe; the second retainer has a projecting portion projecting outward from the connecting mouthpiece and engageing with the slot of the connecting cylinder; and the first retainer is adapted to be inserted into the vertical slit when the second connector is fitted to the first connector, and engage with the horizontal slit when the second connector is rotated from the fitting position.

7. The connecting device according to claim 6, wherein said second connector has urging means for urging the connecting cylinder in such a direction that the connecting cylinder is separated from the first end of the communication pipe.

8. The connecting device according to claim 1, wherein said first connector is provided with a sheetlike porous member covering the first end opening of the communication pipe, and a hygroscopic material contained in the first end portion of the communication pipe, the porous member being permeable to gas and not to liquid.

* * * * *